(12) United States Patent
Nakao et al.

(10) Patent No.: US 6,511,454 B1
(45) Date of Patent: Jan. 28, 2003

(54) IRRIGATION/ASPIRATION APPARATUS AND IRRIGATION/ASPIRATION CASSETTE THEREFORE

(75) Inventors: Munehiro Nakao, Toyokawa (JP); Hidenori Kanda, Okazaki (JP); Kiyoshi Makihara, Gamagori (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/321,725

(22) Filed: May 28, 1999

(30) Foreign Application Priority Data

May 29, 1998 (JP) .......................... 10-150084
May 29, 1998 (JP) .......................... 10-150091

(51) Int. Cl.$^7$ .............................................. A61M 1/00
(52) U.S. Cl. ........................ 604/31; 604/131; 604/151; 604/34
(58) Field of Search .................... 604/35, 317, 320, 604/22, 27, 30, 34, 48, 118, 119, 120, 131, 151–153, 250, 247, 31–33; 128/DIG. 13

(56) References Cited

U.S. PATENT DOCUMENTS

| | | | | |
|---|---|---|---|---|
| 4,493,695 A | * | 1/1985 | Cook | 604/27 |
| 4,627,833 A | | 12/1986 | Cook | 604/34 |
| 4,713,051 A | | 12/1987 | Steppe et al. | 604/30 |
| 4,735,610 A | * | 4/1988 | Akkas et al. | 604/119 |
| 4,758,238 A | | 7/1988 | Sundblom et al. | 604/319 |
| 4,963,131 A | * | 10/1990 | Wortrich | 604/34 |
| 5,163,900 A | * | 11/1992 | Wortrich | 604/30 |
| 5,267,956 A | | 12/1993 | Beuchat | 604/30 |
| 5,364,342 A | | 11/1994 | Beuchat et al. | 604/30 |
| 5,436,418 A | | 7/1995 | Tamehira | 200/61.58 R |
| 5,460,490 A | | 10/1995 | Carr et al. | 417/44.2 |
| 5,533,976 A | * | 7/1996 | Zaleski et al. | 604/153 |
| 5,810,766 A | * | 9/1998 | Barnitz et al. | 604/34 |
| 5,810,770 A | * | 9/1998 | Chin et al. | 604/65 |

FOREIGN PATENT DOCUMENTS

| | | |
|---|---|---|
| JP | 3-23061 | 3/1991 |
| JP | 3-49458 | 7/1991 |
| JP | 4-75014 | 11/1992 |
| JP | 6-225903 | 8/1994 |
| JP | 7-313445 | 12/1995 |
| JP | 9-173338 | 7/1997 |
| JP | 2680510 | 8/1997 |
| JP | 2804371 | 7/1998 |

* cited by examiner

*Primary Examiner*—Brian Casler
*Assistant Examiner*—Cris L. Rodriquez
(74) *Attorney, Agent, or Firm*—Finnegan, Henderson, Farabow, Garrett & Dunner, L.L.P.

(57) ABSTRACT

An irrigation/aspiration apparatus for supplying an irrigation fluid from an irrigation source to a surgical site through a surgical instrument to remove the irrigation fluid with residual tissue by aspiration, the apparatus including, a first cassette provided with a first fluid line for supplying the irrigation fluid and a second fluid line for removing the residual tissue by aspiration, and a second cassette attachable to, and detachable from, the first cassette, the second cassette being provided with a connecting fluid line and a coupling member for connecting at least either the first fluid line or the second fluid line to the surgical instrument.

22 Claims, 7 Drawing Sheets

IRRIGATION/ASPIRATION APPARATUS AND IRRIGATION/ASPIRATION CASSETTE THEREFORE

BACKGROUND OF THE INVENTION

1. Field of the Invention

The present invention relates to an irrigation/aspiration apparatus which supplies an irrigation fluid to a surgical site and aspirates the irrigation fluid containing residual tissue. The present invention also relates to an irrigation/aspiration cassette to be attached to the apparatus.

2. Description of Related Art

One conventionally known irrigation/aspiration apparatus supplies an irrigation fluid through an irrigation tube into a surgical site and then the irrigation fluid and residual tissue are removed by suction. In the field of ophthalmological care, the irrigation/aspiration apparatus is utilized in cataract surgery and vitreous surgery. The irrigation fluid from an irrigation fluid source is injected into the surgical site through a surgical instrument such, for example, as a handpiece connected to the irrigation tube. To remove the residual tissue, suction pressure is applied to an aspiration tube connected to the surgical instrument at one end thereby to drain drainage and the residual tissue from the other end of the aspiration tube.

Recently, it has been suggested to house all or part of the irrigation/aspiration tubes. With this type of apparatus taking advantage of the case or the cassette, the whole case is replaced so as to reduce time and effort spent on tubing. Generally, the cassette is thrown away after one use for a sanitary reason.

As for the irrigation/aspiration apparatus used in the field of ophthalmological care, there is an irrigation/aspiration apparatus configured to suit both cataract surgery and vitreous surgery. However, each cassette to perform different surgery is different to suit a surgical instrument used in the surgery, such as a handpiece and the like.

For example, a cassette for cataract surgery is previously provided with a tube and the like for attachment of a surgical handpiece in order to reduce time and effort spent in tubing or to prevent improper tubing. On the other hand, an aspiration tube is provided to a reusable cutter, which is a surgical instrument used in vitreous surgery. Therefore, a cassette for vitreous surgery is not provided with an aspiration tube and the like, but provided with a connector for attachment the cutter via the aspiration tube. For these reasons, manufacturers has been providing cassettes exclusively for each surgical method or each surgical instrument used in the surgery.

However, it is uneconomical both for the manufacturers and users to prepare a whole set of cassettes for each surgical instrument. In addition, it requires time and effort to replace the whole cassette in case of performing different types of surgery alternately. Further, in case of performing both cataract surgery and vitreous surgery on a patient's eye, for the cassette being disposable, both of the cassettes for cataract surgery and vitreous cassette have to be disposed.

Also, in cataract surgery where different handpieces for phacoemulsification and for irrigation/aspiration should be used, it imposes burden on an operator to replace the cassette to which tubes and the like are connected for attachment of the handpiece or to change the tubing arrangement. In addition, if it takes long to change the cassette or the tubes, time spent in the surgery will be disadvantageously prolonged.

SUMMARY OF THE INVENTION

The present invention has been made in view of the above circumstances and has an object to overcome the above problems and to provide an irrigation/aspiration apparatus and an irrigation/aspiration cassette therefore which can be used in surgery easily and economically without the need for replacing the whole cassette regardless of variety of surgical instruments used.

Also, another object of the present invention is to provide an irrigation/aspiration apparatus and an irrigation/aspiration cassette used therefore which are capable of performing surgery efficiently by eliminating the need to change the cassette or the tubing arrangement even in cases where a plurality of handpieces are used.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an irrigation/aspiration apparatus for supplying an irrigation fluid from an irrigation source to a surgical site through a surgical instrument to remove the irrigation fluid with residual tissue by aspiration, the apparatus comprises a first cassette provided with a first fluid line for supplying the irrigation fluid and a second fluid line for removing the residual tissue by aspiration, and a second cassette attachable to, and detachable from, the first cassette, the second cassette being provided with a connecting fluid line and a coupling member for connecting at least either the first fluid line or the second fluid line to the surgical instrument.

In another aspect of the present invention, an irrigation/aspiration cassette for being attached to an irrigation/aspiration apparatus which supplies an irrigation fluid from an irrigation source to a surgical site through a surgical instrument to remove the irrigation fluid with residual tissue by aspiration, the cassette comprises a first cassette provided with a first fluid line for supplying the irrigation fluid and a second fluid line for removing the residual tissue by aspiration and a second cassette attachable to, and detachable from, the first cassette, the second cassette being provided with a connecting fluid line and a coupling member for connecting at least either the first fluid line or the second fluid line to the surgical instrument.

Also, in another aspect of the present invention, an irrigation/aspiration apparatus for supplying an irrigation fluid from an irrigation source to a surgical site through a surgical instrument to remove the irrigation fluid with residual tissue by aspiration, the apparatus comprises a cassette provided with a first fluid line for supplying the irrigation fluid and a second fluid line for removing the residual tissue by aspiration, at least either the first fluid line or the second fluid line includes a plurality of divided fluid lines, and a selector for selecting from a plurality of the divided fluid lines.

Further, in another aspect of the present invention, an irrigation/aspiration cassette for being attached to an irrigation/aspiration apparatus which supplies an irrigation fluid from an irrigation source to a surgical site through a surgical instrument to remove the irrigation fluid with residual tissue by aspiration, the cassette comprises a cassette provided with a first fluid line for supplying the irrigation fluid and a second fluid line for removing the residual tissue by aspiration, at least either the first fluid line or the second fluid line includes a plurality of divided fluid lines.

As described above, according to the present invention, the sub assembly instead of the whole irrigation/aspiration cassette needs to be replaced to correspond to the surgical instrument or the surgical method. Therefore, manufacturing cost and running cost can be reduced. In addition, it is comparatively easy for the operating staff to complete the replacement.

Also as described above, according to the present invention, even in case of using a handpiece by switching a plurality of fluid lines, the fluid lines remain comparatively simple and thus, the tubing arrangement can be easily done.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
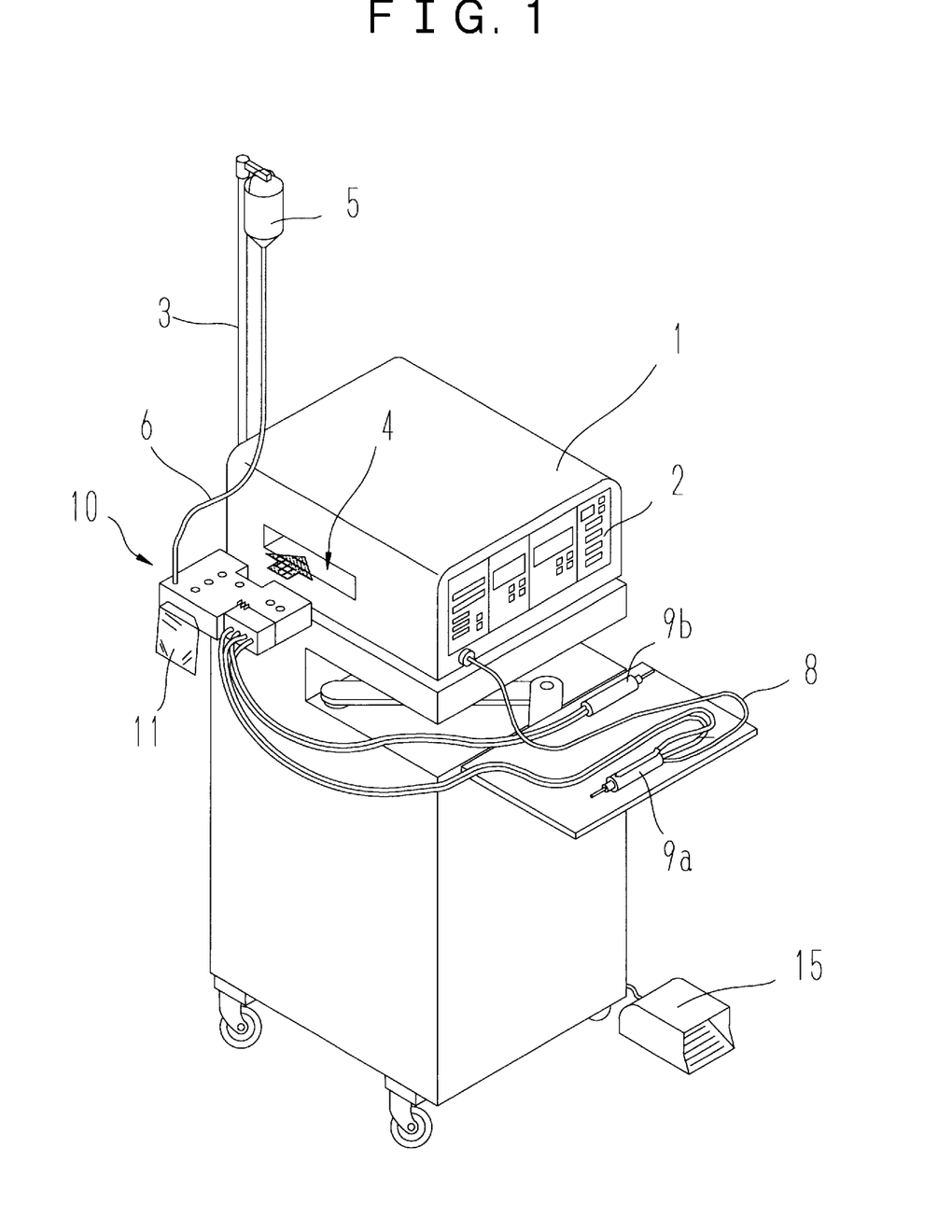
FIG. 1 is a view showing an external representation of an irrigation/aspiration apparatus embodying the present invention.
Figure 2:
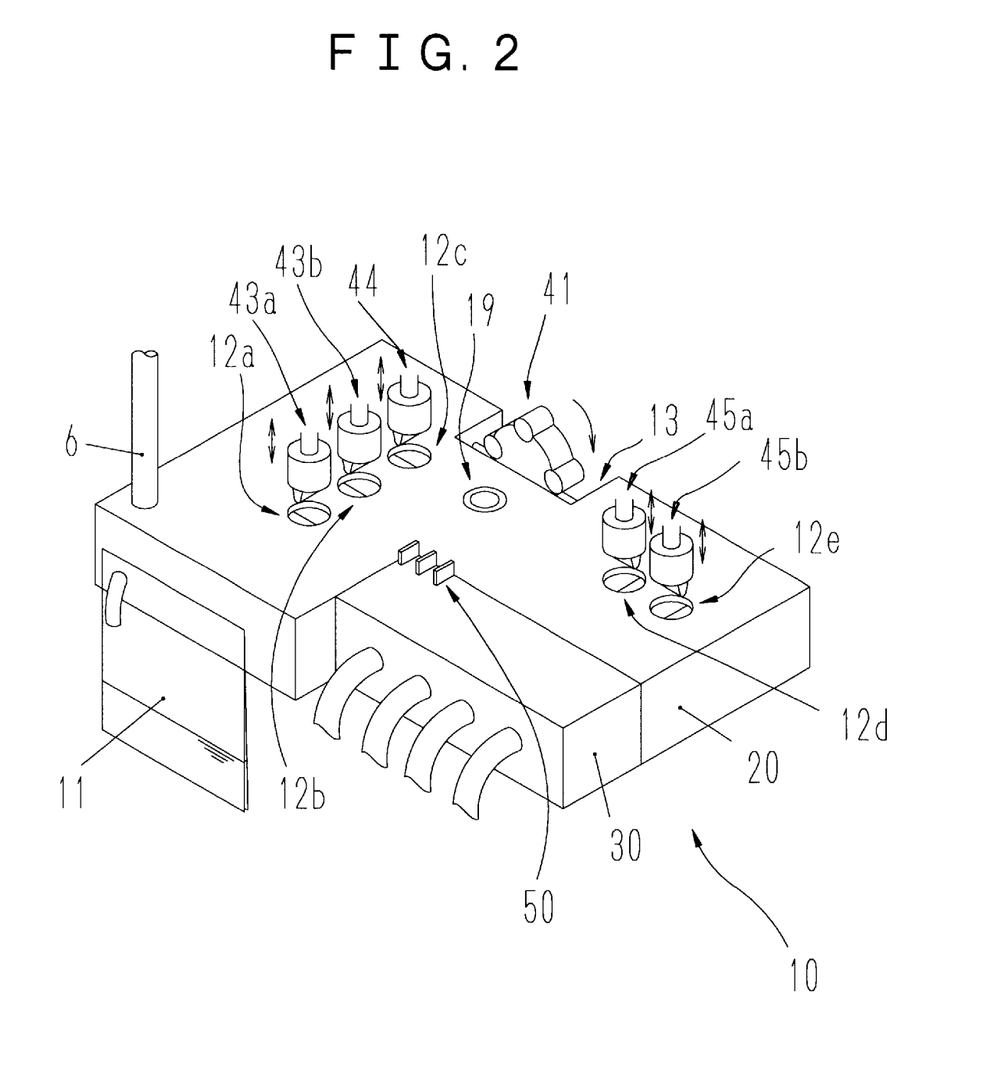
FIG. 2 is a view showing an external representation of an irrigation/aspiration cassette embodying the present invention.
Figure 3:
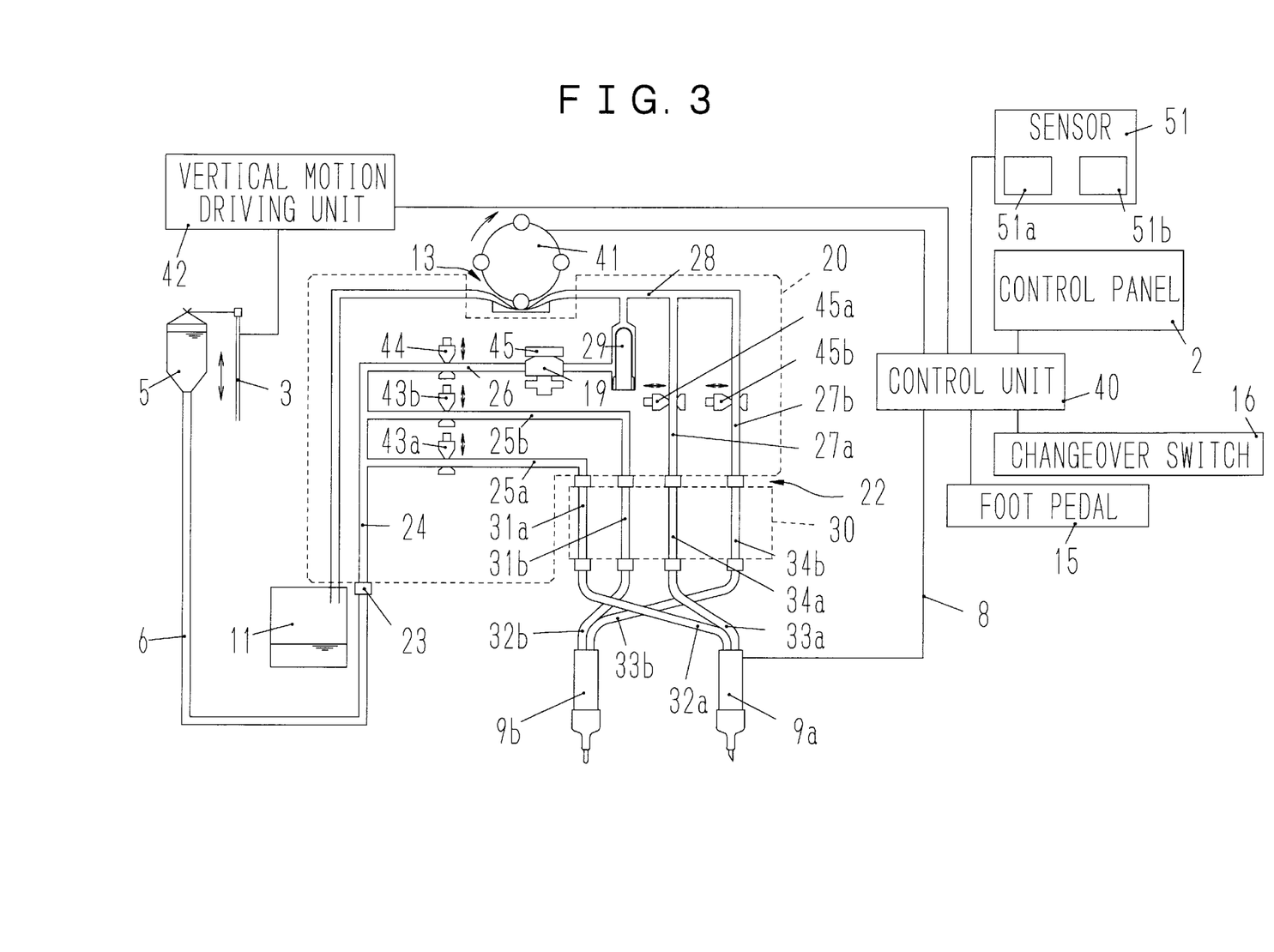
FIG. 3 is a schematic view showing an important part of the irrigation/aspiration apparatus and the irrigation/aspiration cassette shown in FIGS. 1 and 2.

A detailed description of one preferred embodiment of an irrigation/aspiration apparatus and an irrigation/aspiration cassette therefore embodying the present invention will now be given referring to the accompanying drawings. FIGS. 1 and 2 are views respectively showing external representations of an irrigation/aspiration apparatus and an irrigation/aspiration cassette therefore of the preferred embodiment. FIG. 3 is a schematic view showing an important part of the configuration of the apparatus and the cassette.

A main body 1 is provided with a control panel 2, an irrigation pole 3, a cassette receiving portion 4, into which a cassette 10 is inserted, and the like. The cassette 10 will be described in detail hereinafter. A control unit 40 drives and controls a vertical motion driving unit 42 so as to vertically move the pole 3 to a height set with the use of the control panel 2. An irrigation bottle 5 filled with an irrigation fluid is adjusted its height by the vertical movement of the pole 3 thereby to regulate pressure of the irrigation fluid.

The irrigation/aspiration cassette 10 is essentially made up from a main assembly 20 and a sub assembly 30. The main assembly 20 and the sub assembly 30 are detachably connected to each other via a connecting unit 22. The sub assembly 30 is provided in a plurality of different types to suit a surgical instrument used in surgery or the surgical method (as hereinafter described).

An irrigation tube 6 extending from the bottle 5 is connected to the main assembly 20 via an irrigation connecting unit 23. In the main assembly 20, an irrigation fluid line 24 trifurcates (branches) into two irrigation fluid lines: a first irrigation fluid line 25a and a second irrigation fluid line 25b, for providing an irrigation fluid and a bypass fluid line 26 which is connected to an aspiration side. Each of the branch fluid lines are made of pliable tubes having flexibility. Openings 12a, 12b and 12c are formed through a housing of the main assembly 20 at points directly above each fluid line and there is provided a first pinch valve 43a and a second pinch valve 43b for irrigation and a pinch valve 44 for vent on the main body 1. With this configuration, the valves 43a, 43b and 44 are capable of cutting and opening the flow through each tube (the fluid lines 25a, 25b and 26). In this embodiment, each pinch valve is a solenoid valve which opens and closes by electromagnetic operation. The control unit 40 controls each pinch valve inserted into the main assembly 20 through the respective openings 12a–12c so as to accomplish opening and closing of each fluid line selectively by pressing each tube.

The fluid lines 25a and 25b are respectively connected to irrigation fluid line 31a and 31b in the sub assembly 30 via the connecting unit 22. The sub assembly 30 (and a sub assembly 30a) shown in the FIGS. 3 and 4A, for example, is for cataract surgery and has tubes to be connected to an ultrasonic handpiece 9a (hereinafter referred to as US handpiece) to emulsify and aspirate a crystalline lens using ultrasonic vibrations and an irrigation/aspiration handpiece 9b (hereinafter referred to as I/A hand piece). The fluid line 31a is being connected to the irrigation tube 32a at one end for enabling attachment of the US handpiece 9a at the other end. Likewise, the fluid line 31b is being connected to the irrigation fluid line 32b for attachment of the I/A handpiece 9b. In the case of using the US handpiece 9a, the ultrasonic vibrations are controlled by the control unit 40 via a cable 8.

Further, aspiration tubes 33a and 33b are connectable to the US handpiece 9a and the I/A handpiece 9b at one end and are being connected to aspiration fluid lines 34a and 34b at the other end respectively. The fluid lines 34a and 34b are respectively connected to a first aspiration fluid line 27a and a second aspiration fluid line 27b provided in the main assembly 20 via the connecting unit 22. The fluid lines 27a and 27b are also made of tubes having flexibility. As is the case with the irrigation fluid lines, openings 12d, 12e are formed through the housing of the main assembly 20 at points directly above each fluid line and a first pinch valve 45a and a second pinch valve 45b for aspiration are provided on the main body 1. The pinch valves 45a and 45b are capable of cutting and opening the flow through each tube (the fluid lines 27a and 27b). The control unit 40 drives and controls the first pinch valve 45a and the second pinch valve 45b so as to select the fluid line to which aspiration pressure is applied.

The fluid lines 27a and 27b join into a tube 28 with its end extending to a drainage bag 11 to drain drainage out. The tube 28 is partially exposed at an intermediate point through a notch 13 formed in the main assembly 20. That is to say, when the main assembly 20 is inserted into the main body 1, the exposed portion of the tube 28 at the notch 13 is positioned under a driving portion of a peristaltic pump 41 which produces suction. By driving the pump 41, suction pressure is produced within the tube 28 so as to effect aspiration of the drainage from the operative site through the surgical instrument connected thereto via the sub assembly 30.

The tube 28 has a connection upstream from the notch 13 to a balloon portion 29 provided with an air chamber for suppressing pulsation. The balloon portion 29 has a rubber membrane in which air is sealed so as to absorb the pulsation due to producing the suction pressure in the tube by the peristaltic pump 41. The balloon portion 29 is connected to the bypass fluid line 26 at a side thereof. The fluid line 26 is provided, at an intermediate point thereon, with a chamber 19 being in engagement with a pressure sensor 45 of a load detecting type provided on the main body 1. Normally, the pinch valve 44 is closed and the suction pressure produced by the pump 41 is transmitted through the balloon portion 29 to the chamber 19. The chamber 19 is provided with a moving member therein which moves in response to change of the pressure. The sensor 45 detects the suction pressure based on the moving load. When the aspiration is stopped, the pinch valve 44 is opened so as to let the irrigation fluid in the tube 28. As a result, the suction pressure remained in the tube 28 (on the surgical handpiece side from the aspiration/suction pump) is reduced.

As described above, the main assembly 20 has two systems of irrigation fluid lines and aspiration fluid lines respectively. Therefore, by selectively opening and closing the fluid lines, the surgical instruments being connected to the sub assembly 30 can be switched to another suitable for a different surgical operation with ease. For example, the above-mentioned Us handpiece 9a and I/A handpiece 9b are connected to the sub assembly 30. In this case, when the US handpiece 9a is in use, the pinch valves 43a and 45a are opened to allow the flow through the fluid lines 25a and 27a but the pinch valves 43b and 45b are closed to cut the flow through the fluid lines 25b and 27b. When the I/A handpiece 9b is in use, on the other hand, the pinch valves 43b and 45b are opened to allow the flow through the fluid lines 25b and 27b but the pinch valves 43a and 45b are closed to cut the flow through the fluid lines 25a and 27a.

Figure 4A:
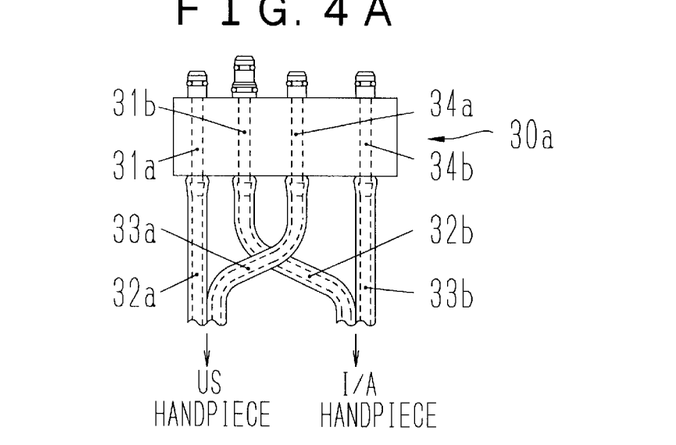
FIGS. 4A–4C are views showing examples of connections to a sub assembly.

Next, a different type of the sub assembly 30 will be described. First, the sub assembly 30a shown in the FIG. 4A is the example for cataract surgery previously described with reference to the FIG. 3.

In this case, for attachment of two kinds of handpieces (US, I/A) for performing irrigation and aspiration, the irrigation tubes 32a and 32b are being connected to the fluid lines 31a and 31b, and the aspiration tubes 33a and 33b are being connected to the fluid lines 34a and 34b respectively beforehand. Generally in cataract surgery, a US handpiece and an I/A handpiece are used alternately. For this reason, it saves trouble of connecting the tubes if both handpieces are connected beforehand. It is also possible to connect an irrigation handpiece (hereinafter referred to as IRR handpiece) instead of either of the two (in this case, the aspiration fluid lines connected to the IRR handpiece are out of use, and thus to be closed).

Figure 4B:
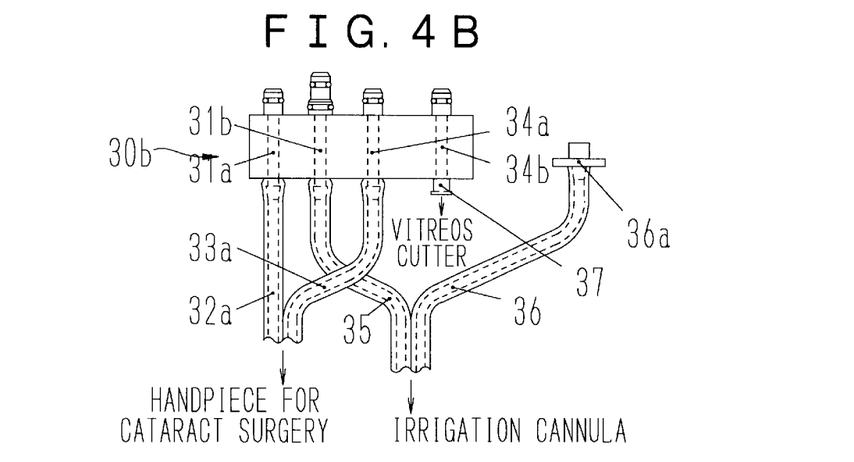

A sub assembly 30b shown in FIG. 4B is an example for cataract surgery and vitreous surgery used in case of performing cataract surgery and vitreous surgery alternately. In the example, the irrigation tube 32a and the aspiration tube 33a for attachment of a handpiece for cataract surgery (the US handpiece 9a or the I/A handpiece 9b) at one end are respectively connected to the fluid line 31a and to the fluid line 34a in the sub assembly 30 at the other end beforehand. Also, the fluid line 31b is connected to an irrigation tube 35 at one end in advance for attachment of an unillustrated irrigation cannula at the other end. The other fluid line 34b is provided with a connector 37 for attachment of an unillustrated vitreous cutter via an aspiration tube. As described, even in the case of performing cataract surgery and vitreous surgery alternately, by connecting surgical instruments for each surgical operation in advance, the trouble of piping arrangement can be avoided.

Figure 4C:
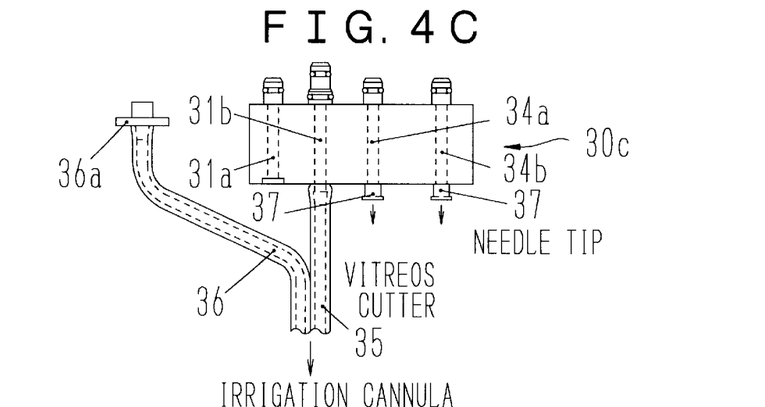

A sub assembly 30c shown in the FIG. 4c is an example for vitreous surgery and the fluid line 31b is being connected beforehand to the irrigation tube 35 for attachment of an irrigation cannula. The fluid lines 34a and 34b are provided with the connectors 37 for attachment of aspiration tubes being connected to a vitreous cutter and to a needle tip for aspiration in vitreous surgery. only one system of irrigation fluid lines is sufficient for vitreous surgery, consequently the fluid line 31a is closed.

The tube 36 shown in the FIGS. 4B and 4C is to vent the air and its connecting terminal 36a is connected to an unillustrated FGX connector to be used in case where air, instead of the irrigation fluid, is sent to the patient's eye.

As described, the cassette 10 is allowed to be divided into the main assembly 20 and the sub assembly 30 and the sub assembly 30 is designed exclusively for each surgical instrument used in cataract surgery or vitreous surgery. In so doing, the main assembly 20 can be commonly used in all surgical operations. This permits reductions in the manufacturing cost of the overall cassette as well as the running cost of the user. In addition, in case of performing cataract surgery and vitreous surgery alternately, for example, only the sub assembly 30, instead of the whole cassette needs to be replaced and thus easily handled. In case of throwing away the cassette after one use, to perform both cataract surgery and vitreous surgery on the patient's eye, one main assembly and two (or possibly more) sub assemblies have to be disposed. Yet, the cost is relatively low as compared with disposing the whole cassette for cataract surgery and another for vitreous surgery.

The main body 1 is further provided with a detecting mechanism to recognize different types of the sub assemblies described above. This detecting mechanism is described hereinafter with reference to the FIG. 5.

Figure 5:
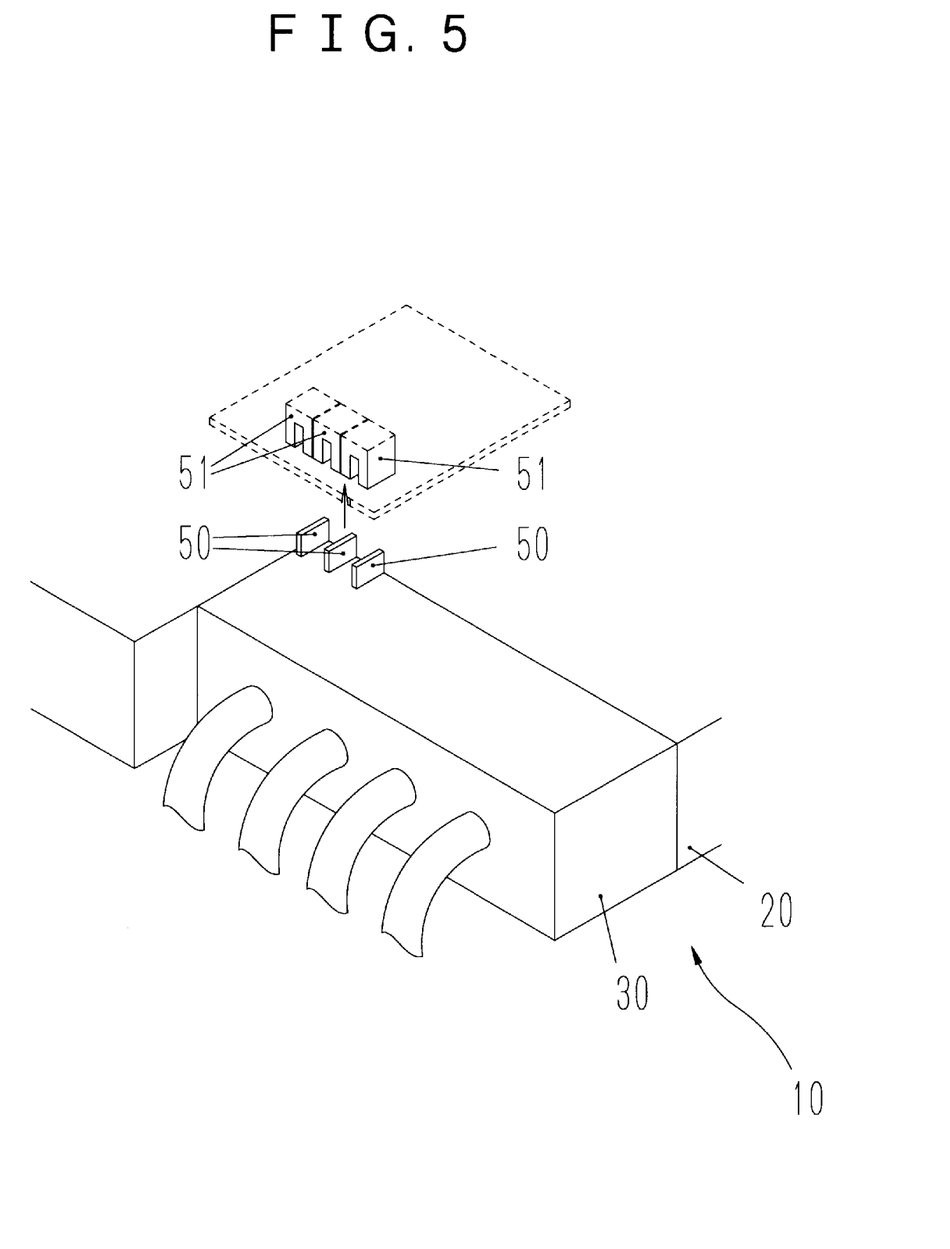
FIG. 5 is a view showing a detecting mechanism which detects a sub assembly.

The sub assembly 30 is provided with a plurality of tags 50 in predetermined positions at the top thereof (the number and the positions of the tags 50 are set differently in accordance with each type of the sub assemblies). When the main assembly 20 and the sub assembly 30 are connected to each other to integrally form the cassette 10 and the cassette 10 is attached to the main body 1 with the use of cassette receiving portion 4, each of the tags 50 is inserted into sensors 51 having a shape of the inverted U provided on the main body 1 (the sensors 51 are set to respond to all the combinations of tags 50, which are different in accordance with each type) Each sensor 51 is comprising a light emitting portion 51a and a light receiving portion 51b provided in opposed positions. Whether or not the light receiving portion 51b detects the light from the light emitting portion 51a allows to detect the presence or absence of each tag 50.

When the tags 50 are inserted, the light from the light emitting portion 51a is cut and consequently the corresponding light receiving portion 51b does not detect the light. Based on signals from the sensors 51 (the light receiving portions 51b), the control unit 40 recognizes that the tags 50 are inserted. The tags 50 are provided in different positions and number in accordance with each type of the sub assembly 30, so that the detection by the sensors 51 allows the apparatus to automatically recognize which type of the sub assembly 30 is being used.

As described above, the type of the sub assembly is automatically detected and recognized thereby to allow automatic setting which is suitable for the surgical instrument corresponding to the type of the sub assembly. In addition, in case of connecting a wrong sub assembly which does not match the surgical method as such, an error signal may be generated to inform of the error or operation signals may be rocked so as to prevent operating errors. Further, it is possible to make automatic setting of parameters in accordance with the sub assembly being connected upon detecting the sub assembly. For example, a US handpiece is connected commonly to the sub assembly provided with two systems of fluid lines for cataract surgery shown in the FIG. 4A and to the sub assembly for cataract surgery and vitreous surgery shown in FIG. 4B. Yet, the aspiration pressure in each surgery is different. Consequently, the automatic setting of the parameters upon connection will reduce the burden imposed on the operator and simplify the setting.

Hereinafter, operations of the apparatus having above-described configuration will be given briefly. The operator integrates the cassette 10 by attaching the suitable sub assembly 30 for the surgery to be performed to the main assembly 20. Thereafter the operator inserts the integrated cassette 10 into the cassette receiving portion 4 provided in the main body 1 (and connects a surgical instrument to the tubes being connected to the sub assembly). upon inserting the cassette 10 into the cassette receiving portion 4, the cassette 10 is moved to a predetermined position in the main body 1 and set in the position. When the cassette 10 is set, the control unit 40 recognizes the type of the sub assembly 30 based on a signal form the sensor 51 and displays the type of the sub assembly 30 on a display of the control panel 2. In addition, conditions such as the aspiration pressure, the amount of aspiration fluid and the like are set as previously determined in accordance with the type of the sub assembly 30. If necessary, these conditions can be changed using the switches provided on the control panel 2.

Changeover between the two systems of the irrigation and aspiration fluid lines (control of each pinch valve) is done by operating a changeover switch 16 provided either on the control panel 2 or on a foot-pedal 15. Since the type of the sub assembly 30 and its combination of fluid lines are found from the signal generated by the sensor 51, the control unit 40 drives and controls each pinch valve to open and close each fluid line.

As described above, operating the changeover switch 16 alone effects changeover among a plurality of hand pieces. This frees the operator from the inconvenience of connecting the tubes and the like, letting the operator concentrate on the surgery. Further, by providing a plurality of irrigation fluid lines and aspiration fluid lines within the detachable cassette, complications in tubing arrangements or setting can be lessened.

Figure 6:
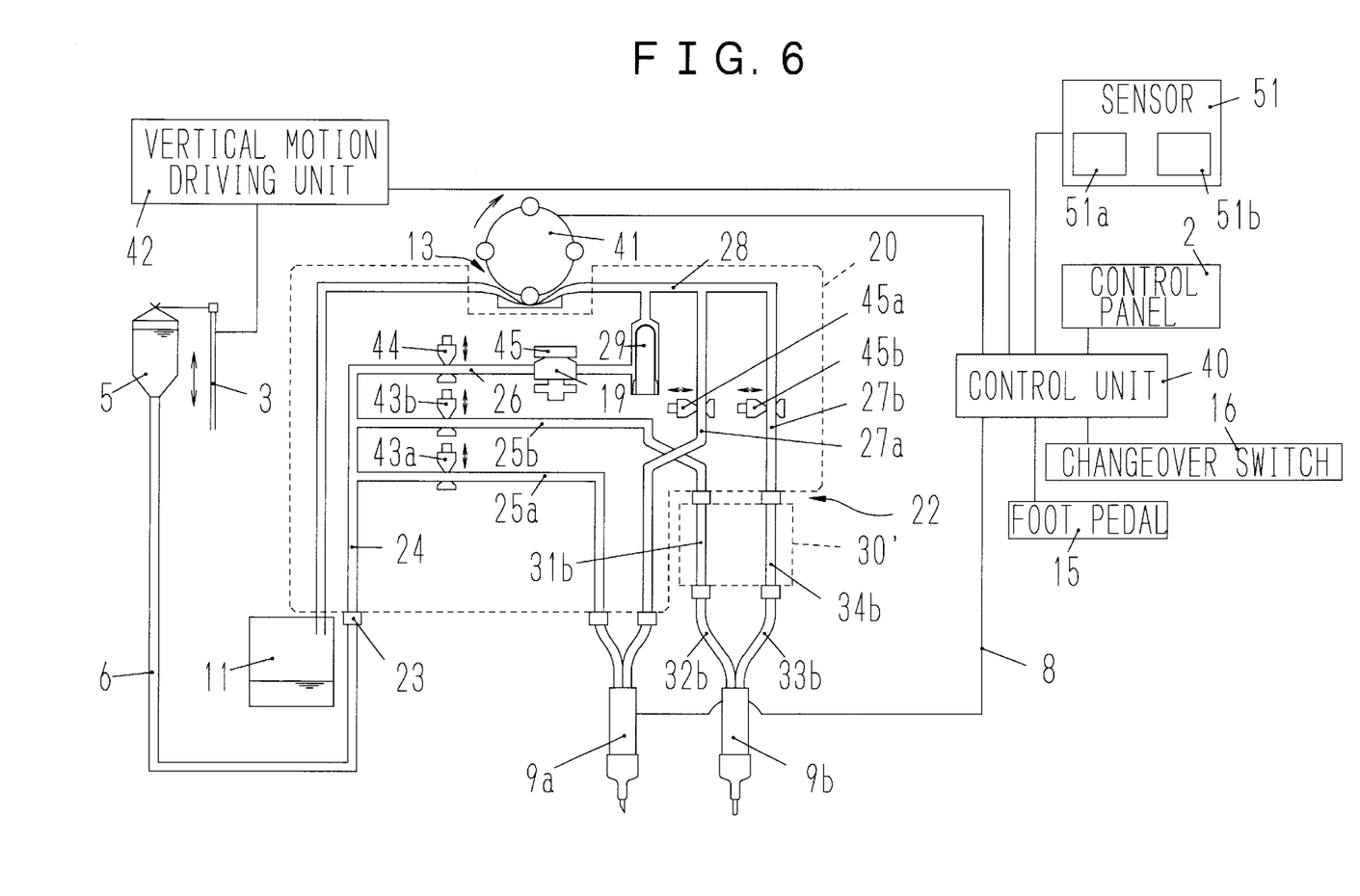
FIG. 6 is a schematic view showing an important part of a modified irrigation/aspiration apparatus and a modified irrigation/aspiration cassette embodying the present invention.
Figure 7A:
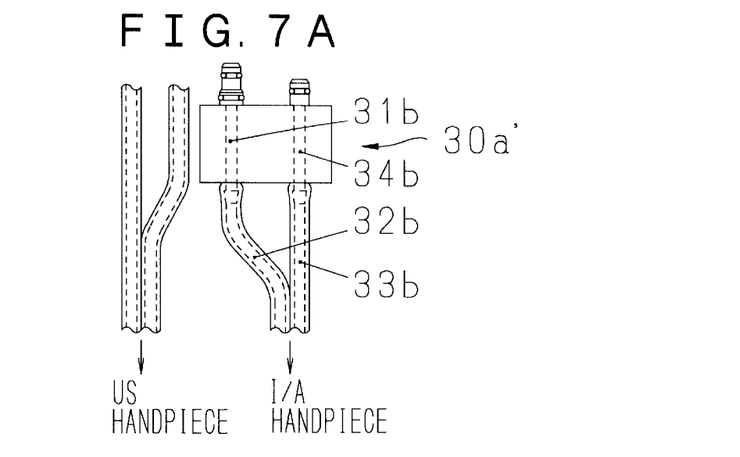
FIGS. 7A–7C are views showing a modified sub assembly applied to the apparatus and the cassette shown in FIG. 6.
Figure 7B:
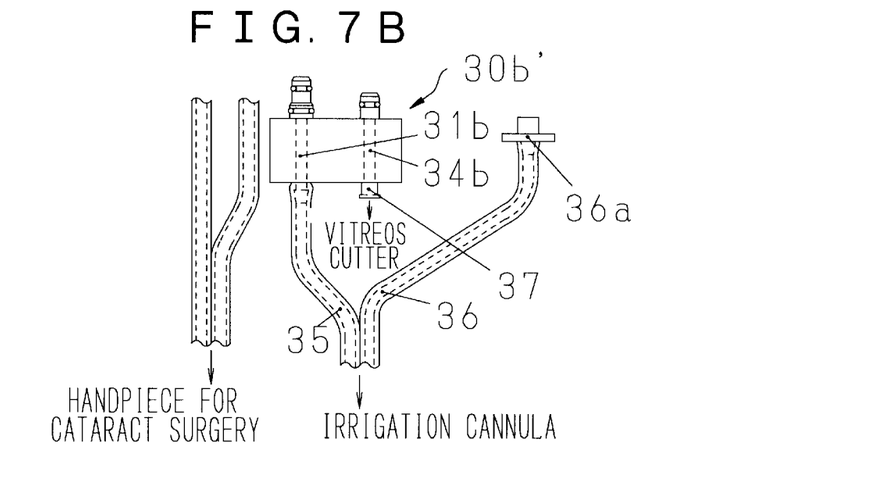
Figure 7C:
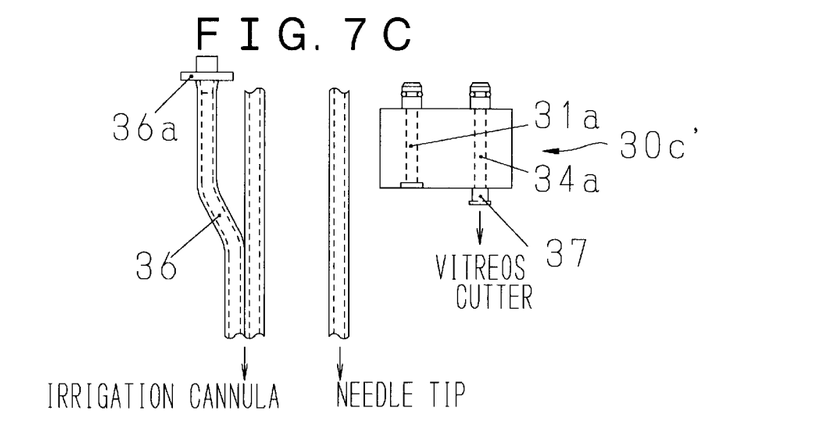

FIGS. 6 and 7 show a modification. In the modification shown in FIG. 6, one of the two irrigation fluid lines and the aspiration fluid lines (the fluid lines 25a and 27a) are connected to a surgical instrument directly from the main assembly 20, while the other irrigation fluid line and the aspiration fluid line (the fluid lines 25b and 27b) are connected to the sub assembly 30' (the fluid lines 31b and 34b). In the case of performing both cataract surgery and vitreous surgery using one and the same apparatus, the US handpiece 9a is kept in connection, and the I/A handpiece 9b needs to be changed to the irrigation cannula and the vitreous cutter. In such a case where one of the surgical instruments is changed more often then the other, this modification may be suitable. Applying this modification will further reduce cost of the sub assembly in comparison with the aforementioned preferred embodiment. FIGS. 7A, 7B and 7C show the modified sub assembly corresponding to the sub assembly shown in FIGS. 4A, 4B and 4C respectively.

Also, another modification may be made to provide one system each for the irrigation fluid line and the aspiration fluid line for enabling attachment of only one surgical instrument. In this modification, providing the sub assembly in wider variety makes it possible to deal with various surgical methods. It goes without saying that the types of the sub assembly are not limited to the ones mentioned in the embodiments described herein.

In the aforementioned embodiments, the detecting mechanism uses the optical sensor. However, a physical or electronic detecting mechanism such as a microswitch or the like may as well be used.

Also, the pinch valves and the vent valves described above are solenoid ones. However, it is possible to use various kinds of valves, for example, a pressure valve by fluid such as air, oil or the like. It is further possible to provide valves within the cassette and connect the valves to the main body via electric connectors thereby to control the valves by the control unit.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An irrigation/aspiration apparatus for supplying an irrigation fluid from an irrigation source to a surgical site through a surgical instrument to remove the irrigation fluid with residual tissue by aspiration, the apparatus comprising:

a first cassette provided with a first fluid line for supplying the irrigation fluid and a second fluid line for removing the residual tissue by aspiration; and a second cassette attachable to, and detachable from, the first cassette, the second cassette being provided with a connecting fluid line and a coupling member for connecting at least either the first fluid line or the second fluid line to the surgical instrument.

2. The irrigation/aspiration apparatus according to claim 1, wherein the second cassette is provided with a plurality of the connecting fluid lines and the coupling members for connecting both of the first fluid line and the second fluid line to the surgical instrument.

3. The irrigation/aspiration apparatus according to claim 1, wherein the coupling member provided in the second cassette includes at least either a tube for connecting the surgical instrument or a connector for connecting a tube which itself is being connected to the surgical instrument.

4. The irrigation/aspiration apparatus according to claim 1, wherein the second cassette is classified into a plurality of varieties by a difference in at least either the connecting fluid line or the coupling member.

5. The irrigation/aspiration apparatus according to claim 4, further comprising a detector for detecting the variety of the second cassette.

6. The irrigation/aspiration apparatus according to claim 5, wherein the second cassette is provided with identifying members for identifying the variety of the second cassette itself, and the detector detects at least either the number or the location of the identifying members.

7. The irrigation/aspiration apparatus according to claim 5, further comprising a controller for setting a condition for surgery in accordance with a result of detection by the detector.

8. The irrigation/aspiration apparatus according to claim 5, further comprising:

a setting device for setting a condition for surgery; and a controller for carrying out at least either announcement to an operator or operational control of the apparatus in accordance with the condition for surgery set by the setting device and a result of detection by the detector.

9. The irrigation/aspiration apparatus according to claim 1, further comprising a connecting device for connecting a main body of the apparatus to the first cassette to which the second cassette is being integrally attached.

10. The irrigation/aspiration apparatus according to claim 1, further comprising a peristaltic pump for producing suction pressure through the second fluid line, and wherein the first cassette is provided with an opening to allow the pump to be in contact with a portion of the second fluid line.

11. The irrigation/aspiration apparatus according to claim 1, wherein at least either the first fluid line or the second fluid line provided in the first cassette includes a plurality of divided fluid lines, and the second cassette is provided with a plurality of the connecting fluid lines and the coupling members to be connected to the divided fluid lines, and the apparatus further comprising a selector for selecting from a plurality of the divided fluid lines.

12. The irrigation/aspiration apparatus according to claim 11, wherein the selector comprises:

an opening and closing device for opening and closing the fluid lines;

an input device for inputting a signal for selection; and a controller for controlling the opening and closing device based on the signal for selection.

13. An irrigation/aspiration cassette for being attached to an irrigation/aspiration apparatus which supplies an irrigation fluid from an irrigation source to a surgical site through a surgical instrument to remove the irrigation fluid with residual tissue by aspiration, the cassette comprising:

a first cassette provided with a first fluid line for supplying the irrigation fluid and a second fluid line for removing the residual tissue by aspiration; and a second cassette attachable to, and detachable from, the first cassette, the second cassette being provided with a connecting fluid line and a coupling member for connecting at least either the first fluid line or the second fluid line to the surgical instrument.

14. The irrigation/aspiration cassette according to claim 13, wherein at least either the first fluid line or the second fluid line provided in the first cassette includes a plurality of divided fluid lines, and the second cassette is provided with a plurality of the connecting fluid lines and the coupling members to be connected to the divided fluid lines.

15. An irrigation/aspiration apparatus for supplying an irrigation fluid from an irrigation source to a surgical site through a surgical instrument to remove the irrigation fluid with residual tissue by aspiration, the apparatus comprising:

a cassette provided with a first fluid line for supplying the irrigation fluid and a second fluid line for removing the residual tissue by aspiration, wherein at least either the first fluid line or the second fluid line includes a plurality of divided fluid lines which are connectable to respective fluid lines of different surgical instruments; and a selector for selecting from the plurality of the divided fluid lines.

16. The irrigation/aspiration apparatus according to claim 15, wherein both the first fluid line and the second fluid line respectively include a plurality of divided fluid lines.

17. The irrigation/aspiration apparatus according to claim 15, wherein the selector selects one of the divided fluid lines to be used.

18. The irrigation/aspiration apparatus according to claim 15, further comprising a connecting device for connecting a main body of the apparatus to the cassette.

19. An irrigation/aspiration apparatus for supplying an irrigation fluid from an irrigation source to a surgical site through a surgical instrument to remove the irrigation fluid with residual tissue by aspiration, the apparatus comprising:

a cassette provided with a first fluid line for supplying the irrigation fluid and a second fluid line for removing the residual tissue by aspiration, wherein at least either the first fluid line or the second fluid line includes a plurality of divided fluid lines; and a selector for selecting from the plurality of the divided fluid lines, the selector comprising:

an opening and closing device for opening and closing the fluid lines;

an input device for inputting a signal for selection; and a controller for controlling the opening and closing device based on the signal for selection.

20. An irrigation/aspiration cassette for being attached to an irrigation/aspiration apparatus which supplies an irrigation fluid from an irrigation source to a surgical site through a surgical instrument to remove the irrigation fluid with residual tissue by aspiration, the cassette comprising:

a first fluid line for supplying the irrigation fluid and a second fluid line for removing the residual tissue by aspiration, wherein at least either the first fluid line or the second fluid line includes a plurality of divided fluid lines which are connectable to respective fluid lines of different surgical instruments.

21. The irrigation/aspiration cassette according to claim 20, further comprising a selector for selecting from a plurality of the divided fluid lines.

22. The irrigation/aspiration cassette according to claim 20, further comprising an opening for leading a selector provided in the irrigation/aspiration apparatus into the cassette to make contact with the divided fluid lines.

* * * * *